United States Patent [19]

Kumagai et al.

[11] Patent Number: 4,581,347

[45] Date of Patent: Apr. 8, 1986

[54] REPLICA COMPOSITION FOR SKIN

[75] Inventors: Hiroko Kumagai, Yokohama; Kazumi Shioya, Tokyo, both of Japan

[73] Assignee: Shiseido Company Ltd., Tokyo, Japan

[21] Appl. No.: 497,955

[22] Filed: May 25, 1983

[30] Foreign Application Priority Data

Sep. 8, 1982 [JP] Japan ................... 57-156337

[51] Int. Cl.$^4$ ........................... A61K 31/695
[52] U.S. Cl. ........................................ 514/63
[58] Field of Search ................... 424/184; 514/63

[56] References Cited

U.S. PATENT DOCUMENTS 4,071,507  1/1978  Schoen ................. 528/355
4,223,122  9/1980  Cella ..................... 528/32
4,302,571  11/1981  Arai et al. ............. 528/32
4,341,888  7/1982  Razzano ................ 528/37

Primary Examiner—Leonard Schenkman
Assistant Examiner—Joseph A. Lipovsky
Attorney, Agent, or Firm—Sprung Horn Kramer & Woods

[57] ABSTRACT

A replica composition suitable for use in the examination of the surface appearance of skin comprising (a) a rubber base containing, as a main ingredient, diorganopolysiloxane, (b) a curing catalyst for curing the rubber base, and (c) a pigment. By using this replica composition, the surface appearance of skin can be directly examined without having to form a positive replica and without causing any irritation to the skin.

10 Claims, 3 Drawing Figures

REPLICA COMPOSITION FOR SKIN

BACKGROUND OF THE INVENTION

1. Field of the Invention

The present invention relates to a replica composition for skin comprising a rubber base containing as, a main ingredient, a diorganopolysiloxane and a curing agent. More specifically, it relates to a replica composition suitable for use in the examination or observation of the microstructure of the surface of skin capable of forming a replica in a short time without causing irritation to the skin.

2. Description of the Prior Art

Heretofore, the surface appearance of human skin has been observed or examined by the following methods:

(a) Direct observation by means of a magnifier (or Lupe) or a microscope;

(b) Indirect observation by the so-called "SUMP (i.e., Suzuki's Universal Micro-Printing)" method, wherein a skin replica is obtained by applying a SUMP plate coated with acetone or amyl acetate to human skin and removing the same, after drying; and (c) Indirect observation by a method wherein a negative replica of human skin is obtained by using a mixture of a rubber base containing, as a main ingredient, diorganopolysiloxane and a curing catalyst and, then, a positive replica is formed from the negative replica (see Japanese Unexamined Patent Publication No. 54-56280).

Method (a) is disadvantageous for the reasons that observation and comparison under uniform conditions are difficult. Therefore, method (b) has been most widely used for the observation of human skin. However, method (b) has problems. For example, stinging, itching, and other skin irritation are caused by the use of the organic solvent; only a flat image (i.e., two-dimensional image) can be obtained by means of a transmission-type microscope as the replica is transparent; and environmental conditions must be carefully maintained for long-term storage of the replica.

The present inventors previously proposed method (c) to solve these problems in the prior art. Method (c) does not cause any irritation to human skin and provides a three-dimensional image suitable for observation having good storage stability. However, this method still has problems in that the operation is troublesome and a relatively long time is required before examination or observation can begin, since a positive replica must be formed from the negative replica.

SUMMARY OF THE INVENTION

Accordingly, the objects of the present invention are to eliminate the problems of the prior art and to provide a replica composition suitable for use in the examination or observation of the surface appearance of skin and capable of forming a stable replica in one short step without causing skin irritation.

Another object of the present invention is to provide a method for directly examining or observing the surface appearance or microstructure of skin without having to form of a positive replica.

Other objects and advantages of the present invention will be apparent from the following description.

In accordance with the present invention, there is provided a replica composition suitable for use in the examination of the surface appearance of skin comprising (a) a rubber base containing, as a main ingredient, diorganopolysiloxane, (b) a curing catalyst for curing the rubber base, and (c) a pigment.

In accordance with the present invention, there is also provided a method for examining the surface appearance of skin comprising the steps of (a) applying, to skin, a replica composition comprising (i) a rubber base containing, as a main ingredient, diorganopolysiloxane, (ii) a curing catalyst for curing the rubber base, and (iii) a pigment; (b) removing the replica from the skin after curing; (c) taking a picture of the resultant replica while the replica is irradiated with light from a direction opposite to the normal sunlight incident direction; and (d) observing the resultant replica developed picture from the reverse direction.

BRIEF DESCRIPTION OF THE DRAWINGS

The present invention will now be illustrated in detail with reference to the accompanying drawings. However, it should be noted that the present invention is not intended to be limited by these drawings.

DESCRIPTION OF THE PREFERRED EMBODIMENTS

Figure 1:
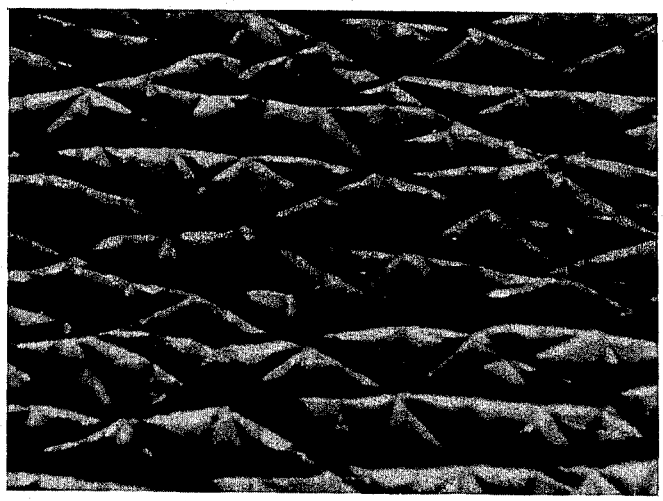
FIG. 1 is a photomicrograph (X 22.5) replica image of the surface appearance (or microstructure) of human facial skin obtained in Example 1 by using a replica composition according to the present invention.

The diorganopolysiloxanes usable as a main ingredient of component (a) of the present replica composition are those having the general formula:

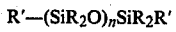

$$R'-(SiR_2O)_n SiR_2 R'$$

wherein R is a monovalent hydrocarbon radical having 1 or 2 carbon atoms, R' is a monovalent hydrocarbon radical having 1 or 2 carbon atoms or a hydroxyl group, and n is an integer of 4 or more, desirably 50 to 2000. The use of dimethylpolysiloxane is especially desirable from the viewpoints of fast curing rate, non-irritation of human skin, and dimensional accuracy of the replica. In the rubber base containing, as a main ingredient, the diorganopolysiloxane, various fillers, such as silica type or calcium carbonate type fillers, and other additives for improving the application touch, such as menthol and peppermint oil, can be included.

The curing catalysts for curing the rubber base containing, as a main ingredient, diorganopolysiloxane include metallic alcoholates and metallic salts of carboxylic acids. Examples of the desirable metals are tin, nickel, cobalt, iron, chromium, zinc, manganese, and aluminum. Examples of the desirable carboxylic acids are lauric acid, stearic acid, and octylic acid. When dimethylpolysiloxane is used as a main ingredient of the rubber base, the use of aluminum isopropylate or dimethyltin dilaurate as a curing catalyst is especially desirable. The curing catalysts can be used in an amount of 0.1 to 2.0 based upon 100 parts by weight of diorganopolysiloxane. The addition amount of the curing catalyst to the rubber base is very small and, therefore, it is difficult to compound an optimum amount of the curing catalyst to the rubber base. Accordingly, the curing catalyst can be desirably dispersed in an oily base such as vaseline prior to the compounding to the rubber base. Furthermore, alkoxysilanes or the hydrolyzates thereof may be generally incorporated into the catlyst to increase the curing rate.

The pigments usable in the replica composition of the present invention are those which do not transmit but reflect light in the replica. Examples of such pigments are white or colored pigments having covering power and not causing any irritation to human skin, as used in cosmetics. Furthermore, the use of pigments providing a skin color to brown replica is desirable. Typical examples of pigments desirably used in the present invention are white pigments such as titanium dioxide and zinc oxide, colored pigments such as iron oxides, and sintered pigments obtained by sintering white pigments and colored pigments at a high temperature. These pigments can be used alone or in any mixture thereof.

These pigments may be previously compounded to the above-mentioned rubber base or the above-mentioned curing catalyst. Alternately, the pigments may be compounded to a mixture of the rubber base and the curing catalyst prior to the curing.

The compounding amount of the pigments to the present replica composition is generally in an amount of 1% to 40% by weight based on the total amount of the replica composition. Less than 1% by weight of a pigment cannot achieve the desired objects of the present invention. Contrary to this, more than 40% by weight of a pigment results in brittleness in the strength of the resultant replica. The particle sizes of the pigments are desirably 20 to 1000 m .

According to the present invention, the surface appearance or microstructure of skin can be advantageously examined without having to form a positive replica, as follows:

The replica composition of the present invention is applied to human skin, for example, a portion of a cheek. Since the curing catalyst is mixed with the rubber base containing diorganopolysiloxane, curing occurs. Accordingly, the curing catalyst should not be mixed with the rubber base until just before the replica composition is applied to the skin.

After applying the replica composition to the skin, the composition is allowed to cure for, generally, 30 seconds to 5 minutes. After curing, the cured replica is removed from the skin. Thus, a negative replica is obtained. Then, the negative replica is directly subjected to microscopic photographing without forming a positive replica. The microscopic picture of the negative replica must be taken while the replica is irradiated with light from a direction opposite to the normal sunlight direction (e.g., with an incident angle of 10° to 50°), i.e., in such a direction that light is applied to the negative replica of the cheek from not the forehead but the jaws. The picture of the replica can be taken by any photographic means. However, a so-called "instant" type camera can be advantageously used for the reason that the replica picture can be observed in situ in a short time.

The picture of the negative replica thus obtained can be observed in such a manner that the picture is positive when the picture is observed reversely in up and down directions. Thus, according to the present invention, the surface appearance or microstructure of human skin can be directly examined without forming a positive replica from a negative replica.

EXAMPLES

The present invention will now be further illustrated by, but by no means limited to, the following examples.

EXAMPLE 1 AND COMPARATIVE EXAMPLES 1 AND 2

Rubber bases and curing catalyst compositions having compositions listed in Table 1 were separately prepared by mixing ingredients in a petri dish with a spatura.

TABLE 1

| Composition | Example 1 | Comparative Examples (% by weight) 1 | 2 |
|---|---|---|---|
| Rubber base | | | |
| Dimethylpolysiloxane | 60 | 60 | 45 |
| Calcium carbonate | — | 16 | 35 |
| Alpha-menthol | 0.1 | 0.1 | 0.1 |
| Spearmint oil | 0.1 | 0.1 | 0.1 |
| Curing agent composition | | | |
| Sintered pigment of titanium oxide and iron oxide (red) | 10 | — | — |
| Dibutyltin laurate | 0.8 | 0.8 | 0.8 |
| Ethyl silicate | 0.4 | 0.4 | 0.4 |
| Vaseline | 20 | 10 | 10 |
| Ethanol | 1.8 | 1.8 | 1.8 |
| Silicon dioxide | 7 | 7 | 7 |

The replica compositions thus prepared were applied to a portion of a cheek. The rubber bases and the catalyst compositions were quickly and thoroughly mixed on a pallet with a spatula just before the replica compositions were applied to the cheek. The replica compositions were coated in a circle having a diameter of 3 cm. The replica compositions were allowed to stand at room temperature for about 2 minutes and, then, the resultant cured rubber-like replicas (negative) were removed from the cheek.

Micrographs of the replicas thus obtained were taken, while light was applied to the replicas from a direction opposite to the normal sunlight direction (i.e., from the jaws with an incident angle of 30°). The micrographs obtained in Example 1 and Comparative Examples 1 and 2 are shown in FIGS. 1, 2, and 3, respectively.

Figure 2:
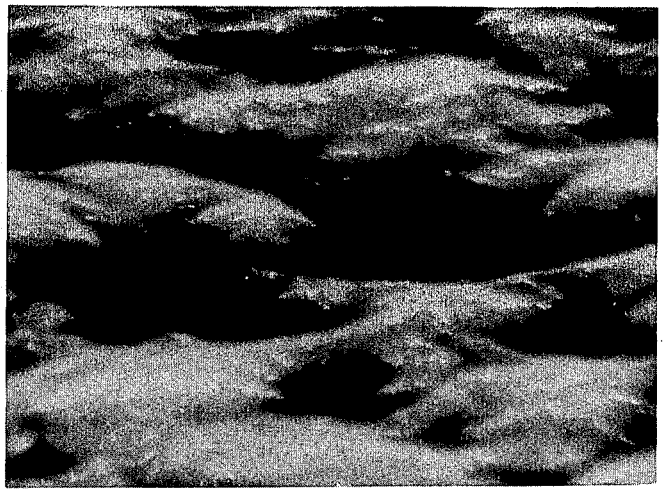
FIG. 2 is a photomicrograph (X 22.5) replica image of the surface appearance of human facial skin obtained in Comparative Example 1.
Figure 3:
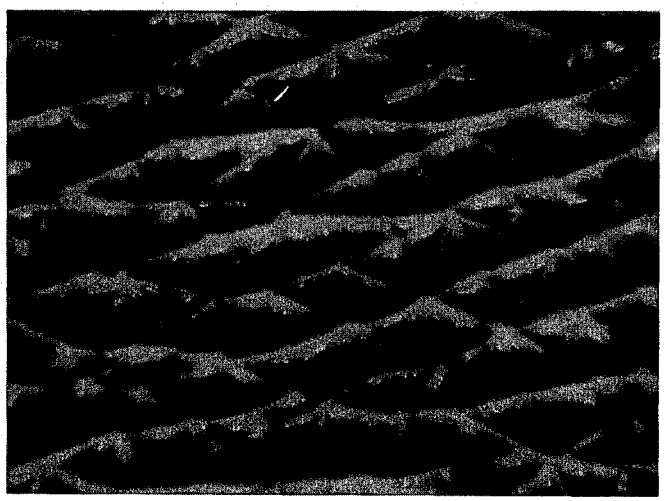
FIG. 3 is a photomicrograph (X 22.5) replica image of the surface appearance of human facial skin obtained in Comparative Example 2.

As is clear from the comparison of FIG. 1 with FIGS. 2 and 3, the conditions of the surface of the cheek can be clearly examined from FIG. 1, whereas the detailed conditions of the surface of the cheek cannot be examined from FIGS. 2 and 3.

EXAMPLES 2 AND 3

Rubber bases and curing catalyst compositions having compositions listed in Table 2 were separately prepared in the same manner as in Example 1.

From these rubber bases and curing catalyst compositions, negative micrographs which can be seen as positive micrographs and which clearly show the detailed conditions of the surface appearance of a cheek as in Example 1 were obtained.

TABLE 2

| Composition | Example 2 | (% by weight) Example 3 |
|---|---|---|
| Rubber base | | |
| Dimethylpolysiloxane | 64 | 45.2 |
| Diatomite | 16 | — |
| Titanium dioxide | 2 | 35 |
| Iron oxide (red:yellow:black = 4:5:1) | 0.2 | 2 |

TABLE 2-continued

| Composition | Example 2 | (% by weight) Example 3 |
|---|---|---|
| Alpha-menthol | 0.1 | 0.1 |
| Spearmint oil | 0.1 | 0.1 |
| Curing agent composition | | |
| Aluminum isopropylate | 3 | 3 |
| Vaseline | 9.8 | 9.8 |
| Polyethylene silicate | 5 | 5 |

While the present invention has been described in terms of its specific embodiments concerning the application to human skin, certain modifications can be made by those skilled in the art. For example, the present replica composition can be applied to form a replica of hair and animal skin. Furthermore, the present replica composition can be utilized in the production of surface materials for making dolls or show window dummies.

We claim:

1. A method of making a photograph of a quality suitable for examining the surface appearance of human skin comprising the steps of:
   (a) applying, to skin, a replica composition comprising (i) a rubber base containing, as a main ingredient, diorganopolysiloxane, (ii) a curing catalyst in an amount of 0.1 to 2.0 parts by weight based on 100 parts by weight of diorganopolysiloxane and (iii) 1 to 40% of a pigment based on the weight of the composition;
   (b) removing the replica from the skin after curing; and
   (c) taking a picture of the resultant replica while the resultant replica is irradiated with light from a direction opposite to the normal sunlight incident direction.

2. A method as claimed in claim 1, wherein said diorganopolysiloxane is dimethylpolysiloxane.

3. A method as claimed in claim 1, wherein said curing catalyst is a metallic alcoholate.

4. A method as claimed in claim 3, wherein said metallic alcoholate is aluminum propylate.

5. A method as claimed in claim 1, wherein said curing catalyst is a metallic salt of a carboxylic acid.

6. A method as claimed in claim 5, wherein said metallic salt of the carboxylic acid is dibutyltin laurate.

7. A method as claimed in claim 1, wherein said curing catalyst is dispersed in an oily base.

8. A method as claimed in claim 1, wherein said pigment is not light transmittable.

9. A method as claimed in claim 1, wherein the replica composition is in the form of two components, ingredient (iii) being premixed with (i) or (ii) as one of the components.

10. A method according to claim 9, (iii) being premixed with (ii).

* * * * *